United States Patent [19]

Reinherz et al.

[11] Patent Number: 5,109,123
[45] Date of Patent: Apr. 28, 1992

[54] ALTERATION OF ABILITY OF SOLUBLE CD4 FRAGMENTS TO BIND HIV

[75] Inventors: Ellis L. Reinherz, Lincoln; Linda K. Clayton, Jamaica Plain, both of Mass.

[73] Assignee: Dana Farber Cancer Institute, Boston, Mass.

[21] Appl. No.: 217,475

[22] Filed: Jul. 11, 1988

Related U.S. Application Data

[63] Continuation-in-part of Ser. No. 206,585, Jun. 14, 1988, which is a continuation-in-part of Ser. No. 144,313, Jan. 14, 1988, abandoned, which is a continuation-in-part of Ser. No. 106,185, Oct. 8, 1987, abandoned.

[51] Int. Cl.[5] .................. C07H 15/12; C12N 15/00
[52] U.S. Cl. ................................ 536/27; 435/91; 435/172.3; 435/235.1; 935/1; 935/9; 935/10; 935/11; 935/12; 935/65
[58] Field of Search ............... 435/91, 172.3, 235; 935/9, 10, 11, 12, 65; 536/27

[56] References Cited

PUBLICATIONS

Maddon et al., PNAS 84:9155-9159, 1987.
Maddan et al. (el) 42:93-104, 1985.
Stephens et al., Cell 47:1053-1059, 1986.
Siliciano et al., *Cell*, 54: 561-575 (1988).
Fisher et al., *Nature*, 331: 76-78 (1988).
Hussey et al., *Nature*, 331: 78-81 (1988).
Deen et al., *Nature*, 331: 82-84 (1988).
Traunecker et al., *Nature*, 331: 84-86 (1988).
Berger et al., *Proc. Natl. Acad. Sci. USA*, 85: 2357-2361 (1988).
Bertonis et al., Abstract Cold Spring Harbor Laboratory, Sep. 1987.
McDougal, J. S. et al., *UCLA Symposia on Mol. and Cell Biol.* vol. 71–Human Retroviruses, Cancer and AIDS, pp. 269-281 Dec. 1987.
Dalgleish, A. G. et al., UCLA Symposia on Mol. and Cell Biol., vol. 71, pp. 283-288, Dec. 1987.
McDougal, J. S. et al., Cold Spring Harbor Symposia on Quantitative Biol., 51: 703-712 (1986).
Maddon et al., *Cell*, 42, 93-104 (1985).

*Primary Examiner*—Robin L. Teskin
*Assistant Examiner*—Beth A. Burrous
*Attorney, Agent, or Firm*—Hamilton, Brook, Smith & Reynolds

[57] ABSTRACT

DNA encoding modified soluble human CD4 fragments whose ability to bind to the HIV gp120 envelope protein is different from the ability of soluble human CD4 fragments; modified soluble human CD4 fragments having altered gp120 binding ability, methods of making such fragments and methods of using such fragments.

1 Claim, 9 Drawing Sheets

FIG. 1a

```
         AGAAAGTGGTGCTGGGCAAAAAAGGGATACAGTGGAACTGACCTGTACAGCTTCCCAG          60 bp
         ---------+---------+---------+---------+---------+---------+
         TTCTTTCACCACGACCCGTTTTTTCCCTATGTCACCTTGACTGGACATGTCGAAGGGTC k  k  v  v  l  g  k  k  g  d  t  v  e  l  t  c  t  a  s  q         20 aa
         ---------+---------+---------+---------+---------+---------+

AAGAAGAGCATACAATTCCACTGGAAAAACTCCAACCAGATAAAGATTCTGGGAAATCAG         120
         ---------+---------+---------+---------+---------+---------+
         TTCTTCTCGTATGTTAAGGTGACCTTTTTGAGGTTGGTCTATTTCTAAGACCCTTTAGTC k  k  s  i  q  f  h  w  k  n  s  n  q  i  k  i  l  g  n  q         40
         ---------+---------+---------+---------+---------+---------+

GGCTCCTTCTTAACTAAAGGTCCATCCAAGCTGAATGATCGCGCTGACTCAAGAAGAAGC         180
         ---------+---------+---------+---------+---------+---------+
         CCGAGGAAGAATTGATTTCCAGGTAGGTTCGACTTACTAGCGCGACTGAGTTCTTCTTCG g  s  f  l  t  k  g  p  s  k  l  n  d  r  a  d  s  r  r  s         60
         ---------+---------+---------+---------+---------+---------+

CTTTGGGACCAAGGAAACTTCCCCCTGATCATCAAGAATCTTAAGATAGAAGACTCAGAT         240
         ---------+---------+---------+---------+---------+---------+
         GAAACCCTGGTTCCTTTGAAGGGGACTAGTAGTTCTTAGAATTCTATCTTCTGAGTCTA l  w  d  q  g  n  f  p  l  i  i  k  n  l  k  i  e  d  s  d         80
         ---------+---------+---------+---------+---------+---------+
```

FIG. 1b

```
ACTTACATCTGTGAAGTGGAGGACCAGAAGGAGGAGGTGCAATTGCTAGTGTTCGGATTG       300
---+---:---+---:---+---:---+---:---+---:---+---:---+---:---+
TGAATGTAGACACTTCACCTCCTGGTCTTCCTCCTCCACGTTAACGATCACAAGCCTAAC
 t  y  i  c  e  v  e  d  q  k  e  e  v  q  l  v  f  g  l       100

ACTGCCAACTCTGACACCCACCTGCTTCAGGGGCAGAGCCTGACCCTTGACCCTTGGAGAGC    360
---+---:---+---:---+---:---+---:---+---:---+---:---+---:---+
TGACGGTTGAGACTGTGGGTGGACGAAGTCCCCGTCTCGGACTGGGAACCTCTCG
 t  a  n  s  d  t  h  l  q  g  q  s  l  t  l  e  s              120

CCCCCTGGTAGTAGCCCCTCAGTGCAATGTAGGAGTCCAAGGGGTAAAAACATACAGGGG    420
---+---:---+---:---+---:---+---:---+---:---+---:---+---:---+
GGGGGACCATCATCGGGGAGTCACGTTACATCCTCAGGTTCCCCATTTTTGTATGTCCCC
 p  p  g  s  s  p  s  v  q  c  r  s  p  r  g  k  n  i  q  g    140

GGGAAGACCCTCTCCGTGTCTCAGCTGGAGCTCCAGGATAGTGGCCACCTGGACATGCACT    480
---+---:---+---:---+---:---+---:---+---:---+---:---+---:---+
CCCTTCTGGGAGAGGCACAGAGTCGACCTCGAGGTCCTATCACCGTGGACCTGTACGTGA
 g  k  t  l  s  v  s  q  l  e  l  q  d  s  g  t  w  t  c  t    160
```

FIG. 1c

```
GTCTTGCAGAACCAGAAGAAGGTGGAGTTCAAAATAGACATCGTGGTGCTAGCTTTCCAG    540
---------+---------+---------+---------+---------+---------+
CAGAACGTCTTGGTCTTCTTCCACCTCAAGTTTTATCTGTAGCACCACGATCGAAAGGTC
     v  l  q  n  q  k  k  v  e  f  k  i  d  i  v  v  l  a  f  q    180

AAGGCCCTCCAGCATAGTCTATAAGAAAGAGGGGGAACAGGTGGAGTTCTCTCCCCACTC    600
---------+---------+---------+---------+---------+---------+
TTCCGGGAGGTCGTATCAGATATTCTTTCTCCCCCTTGTCCACCTCAAGAGAAGGGGTGAG
     k  a  s  s  i  v  y  k  k  e  g  e  q  v  e  f  s  f  p  l    200

GCCTTTACAGTTGAAAAGCTGACGGGCAGTGGCGAGCTGTGGTGGCAGGCGGAGAGGGCT    660
---------+---------+---------+---------+---------+---------+
CGGAAATGTCAACTTTTCGACTGCCCGTCACCGCTCGACACCACCGTCCGCCTCTCCCGA
     a  f  t  v  e  k  l  t  g  s  g  e  l  w  w  q  a  e  r  a    220

TCCTCCTCCAAGTCTTGGATCACCTTTGACCTGAAGAACAAGGAAGTGTCTGTAAAACGG    720
---------+---------+---------+---------+---------+---------+
AGGAGGAGGTTCAGAAGCCTAGTGGAAACTGGACTTCTTGTTCCTTCACAGACATTTTGCC
     s  s  s  k  s  w  i  t  f  d  l  k  n  k  e  v  s  v  k  r    240
```

FIG. 1d

```
GTTACCCAG GACCCTAAGCTCCAGATGGGCAAGAAGCTCCCGCTCCACCCTGCCC
        |----+----|----+----|----+----|----+----|----+----|  780
CAATGGGTC CTGGGATTCGAGGTCTACCCGTTCTTCGAGGGCGAGGTGGGACGGG
 v  t  q  d  p  k  l  q  m  g  k  k  l  p  l  h  l  t  l  p   260

CAGGCCTTGCCTCAGTATGCTGGCTCTGGAAAACCTCACCCTGGCCCTTGAAGCGAAAACA
|----+----|----+----|----+----|----+----|----+----|----+----|  840
GTCCGGAACGGAGTCATACGACCGAGACCTTTTGGAGTGGGACCGGGAACTTCGCTTTTGT
 q  a  l  p  q  y  a  g  s  g  n  l  t  l  a  l  e  a  k  t   280

GGAAAGTTGCATCAGGAAGTGAACCTGGTGGTGATGAGAGCCACTCAGCTCCAGAAAAAT
|----+----|----+----|----+----|----+----|----+----|----+----|  900
CCTTTCAACGTAGTCCTTCACTTGGACCACCACTACTCTCGGTGAGTCGAGGTCTTTTTA
 g  k  l  h  q  e  v  n  l  v  v  m  r  a  t  q  l  q  k  n   300

TTGACCTGTGAGGTGTGGGGACCCACCTCCCCCTAAGCTGATGCTGAGCTTGAAACTGGAG
|----+----|----+----|----+----|----+----|----+----|----+----|  960
AACTGGACACTCCACACCCCTGGGTGGAGGGGATTCGACTACGACTCGAACTTTGACCTC
 l  t  c  e  v  w  g  p  t  s  p  k  l  m  l  s  l  k  l  e   320
```

FIG. 1e

```
AACAAGGAGGCAAAGGTCTCGAAGGCGGGAGAAGGCGGTGTGGGTGCTGAACCCTGAGGCG
---:---+---:---+---:---+---:---+---:---+---:---+   1020
TTGTTCCTCCGTTTCCAGAGCTTCGCCCTCTTCCGCCACACCCACGACTTGGGACTCCGC
---:---+---:---+---:---+---:---+---:---+---:---+
 n  k  e  a  k  v  s  k  r  e  k  a  v  w  v  l  n  p  e  a   340
---:---+---:---+---:---+---:---+---:---+---:---+

GGGATGTGGCAGTGTCTGCTGAGTGACTCGGGACAGGTCCTGCTGGAATCCAACATCAAG
---:---+---:---+---:---+---:---+---:---+---:---+   1080
CCCTACACCGTCACAGACGACTCACTGAGCCCTGTCCAGGACGACCTTAGGTTGTAGTTC
---:---+---:---+---:---+---:---+---:---+---:---+
 g  m  w  q  c  l  l  s  d  s  g  q  v  l  e  s  n  i  k    360
---:---+---:---+---:---+---:---+---:---+---:---+

GTTCTGCCCACATGGTCCACCCCGGTT CATTAA
---:---+---:---+---:---+---:---+---:---+--     1113
CAAGACGGGTGTACCAGGTGGGGCCAA GTAATT
---:---+---:---+---:---+---:---+---:---+--
 v  l  p  t  w  s  t  p  v   h  .                370
---:---+---:---+---:---+---:---+---:---+--
```

ALTERATION OF ABILITY OF SOLUBLE CD4 FRAGMENTS TO BIND HIV

RELATED APPLICATIONS

This application is a continuation-in-part application of U.S. Ser. No. 206,585, filed Jun. 14, 1988, which is a continuation-in-part application of U.S. Ser. No. 144,313, filed Jan. 14, 1988, now abandoned, which is a continuation-in-part application of U.S. Ser. No. 106,185, filed Oct. 8, 1987. The teachings of the three related applications are incorporated herein by reference.

BACKGROUND

The CD4 (T4 molecule, which is a surface glycoprotein on a subset of T lymphocytes (referred to as T4 lymphocytes) is involved in Class II (Ia) MHC recognition and appears to be the physiological receptor for one or more monomorphic regions of class II MHC. Meuer, S. et al., *Proceedings of the National Academy of Sciences, U.S.A.*, 79:4395-4399 (1982); Biddison, W. et al., *J. Exp. Med.*, 156:1065-1076 (1982); Gay, D. et al., *Nature*, 328: 626-629 (1987).

Human CD4 is also the receptor for the gp120 envelope glycoprotein of the human immunodeficiency virus (HIV) and is essential for virus entry into the host cell, and for membrane fusion, which both contribute to cell-to-cell transmission of the virus and to its cytopathic effects. Klatzmann, D., et al., *Science*, 225: 59-63 (1984); Dalgleish, A. G., et al., *Nature*, 312: 763-766 (1984); Sattentau, Q., et al., *Science*, 234: 1120-1123 (1986); McDougal, J. S., et al., *J. Immunol.*, 137: 2937-2944 (1986); McDougal, J. S. et al., *Science*, 231: 382-385 (1986); Maddon, P. J., et al., *Cell*, 47: 333-348 (1986); Sodroski, J., et al., *Nature*, 322: 470-474 (1986); Lifson, J., et al., *Nature*, 323: 725-728 (1986). Sequence analysis of CD4 has suggested an evolutionary origin from a structure with four immunoglobulin-related domains. Clark, S., et al. *Proc. Natl. Acad. Sci.*, 84: 1649-1653 (1987); Littman, D. R., et al., *Nature*, 325: 453-455 (1987). Only the two $NH_2$-terminal domains are required to mediate HIV gp120 binding. Traunecker, A., et al., *Nature*, 331: 84-86 (1988); Berger, E. A., et al. *Proc. Natl. Acad. Sci. USA*, 85: 2357-2361 (1988); Richardson, N. E., et al., *Proc. Natl. Acad. Sci. USA*, in press.

Considerable effort has been expended in studying the CD4-gp120 interaction and in trying to interfere with or inhibit that interaction, in an attempt to provide a means by which the life threatening effects of HIV infection can be slowed or reversed. Several groups have focused their efforts on the ability of soluble CD4 (T4) protein to interfere with infection of cells by HIV and its subsequent effects. Hussey, R. E. et al., *Nature*, 331:78-81 (1988); Fisher, R. A. et al., *Nature*, 331:76-78 (1988); Deen, K. C. et al., *Nature*, 331:82-84 (1988); Traunecker, A. et al., *Nature*, 331:84-86 (1988). A means by which to prevent HIV infection of T4 lymphocytes (i.e., helper and inducer T lymphocytes), which make up approximately 60-80% of the total circulating T lymphocyte population, would be of great value, particularly in light of the fact that HIV infection of such cells can cause total collapse of the immune system. Curran, J. et al., *Science*, 229:11352-1357 (1985); Weiss, R. et al., *Nature*, 324:572-575 (1986).

SUMMARY OF THE INVENTION

The present invention relates to DNA encoding modified soluble human CD4 fragments whose ability to bind to the HIV gp120 envelope protein (gp120) is different from the ability of soluble human CD4 fragments to bind such CD4 fragments, and to a method of modifying or altering the ability of a soluble human CD4 fragment to bind HIV gp120. Such fragments are referred to as modified soluble human CD4 fragments having altered gp120 binding ability. The present invention further relates to use of those CD4 fragments to interfere with HIV entry into cells.

In particular, this invention relates to modified soluble human CD4 fragments in which the amino acid sequence of soluble human CD4 is altered at a selected site or sites in such a manner that the resulting CD4 fragment has gp120 binding ability or affinity less than that of the corresponding (unaltered) soluble human CD4 fragment or gp120 binding ability or affinity greater than that of the corresponding (unaltered) human CD4 fragment. Such fragments are referred to, respectively, as modified soluble human CD4 fragments with diminished gp120 binding ability and modified soluble human CD4 fragments with enhanced gp120 binding ability.

Soluble human CD4 fragments include none of the hydrophobic transmembrane region of CD4 or only a portion (generally six amino acids or less) of the hydrophobic region which does not prevent solubilization of the fragments. CD4 fragments with altered gp120 binding ability differ from such soluble human CD4 fragments in that the amino acid sequences of the CD4 fragments with altered gp120 binding ability are different from the amino acid sequence of the soluble CD4 protein at a site or sites which have been found to be critical for gp120 binding. Until the present time, it has not been possible to selectively alter gp120 binding ability of soluble CD4 fragments because sites critical to gp120 binding had not been identified. Such critical sites have now been identified by means of oligonucleotide-directed mutagenesis and have been found to occur in domain I and domain II of human CD4 protein, suggesting that the gp120 binding site is complex and involves both of the $NH_2$-terminal domains. Modifications of the T4 cDNA, as it is represented in FIG. 1, have been made and the encoded CD4 fragments expressed. Resulting CD4 fragments have been shown to have altered gp120 binding ability in vitro; in these instances, gp120 binding ability has been abrogated. Modifications at these same sites, and at other, as yet unidentified, sites can similarly be made to enhance gp120 binding ability, as well as to reduce or turn down (but not eliminate) gp120 binding ability.

Such modified soluble CD4 fragments with altered gp120 binding ability can be used for diagnostic, therapeutic and preventive purposes. For example, such fragments having enhanced gp120 binding ability can be used to determine the presence or absence of gp120 in a biological sample (e.g., blood, urine, saliva, semen) and, thus, to determine whether HIV is present in the sample or not. In addition, they can be used to treat individuals infected with HIV, in vivo (e.g., by administration to infected individuals). They can also be used prophylactically. That is, they can be administered to individuals at risk for HIV infection. Further, they can be used to prevent infection by HIV by, for example, being coated onto materials used as barriers against introduction of the virus (e.g., condoms, spermicides, garments, containers for collecting, processing or storing blood, etc.).

BRIEF DESCRIPTION OF THE DRAWINGS

FIG. 1 (parts a-e) is the nucleotide sequence of T4 SEC cDNA (referred to as the $T4_{ex1}$ sequence), which encodes 370 amino acids of soluble CD4 protein (referred to as $T4_{ex1}$); the deduced amino acid sequence of the $T4_{ex1}$ protein is represented below the nucleotide sequence.

DETAILED DESCRIPTION OF THE INVENTION

The present invention is based on identification of amino acid residues of (or sites of) human CD4 protein which are critical for binding to HIV gp120. These sites have been precisely defined through oligonucleotide-directed mutagenesis used to create mutant human CD4 molecules which include from 1-4 amino acid substitutions. The approach used in defining such sites has taken advantage of the differences known to exist in the amino acid sequences of the extracellular segment of murine CD4 and that of its human counterpart.

Identification of Amino Acid Residues of Human CD4 Critical for qp120 binding The extracellular segment of murine CD4 is overall 50% identical to its human counterpart (Maddon, P. J. et al., Proc. Natl. Acad. Sci. USA, 84: 9155-9159 (1987) at the amino acid (a.a.) level but fails to bind gp120. McClure, M. O., et al., Nature, 330: 487-489 (1987) These differences were used in precisely defining those residues of human CD4 critical for gp120 binding. Substitutions of all non-conserved murine for human CD4 residues between amino acid positions 27-167 were made. To this end, oligonucleotide-directed mutagenesis was used to create each of 16 individual mutant human CD4 molecules containing from 1 to 4 amino acid substitutions. Introduction of as few as three amino acids into corresponding positions of human CD4 resulted in CD4 fragments unable to bind gp120. These critical residues have been shown to be located in domain I as well as in domain II of CD4, thus implying that the gp120 binding site is complex and involves both of the NH$_2$-terminal domains. Modelling studies using the 3-dimensional coordinates of the $V_k$ Bence-Jones homodimer, REI, localize the site of domain I to the $C''\beta$ strand. Thus domain I is distant from the loops analogous to hypervariable regions.

Figure 2:
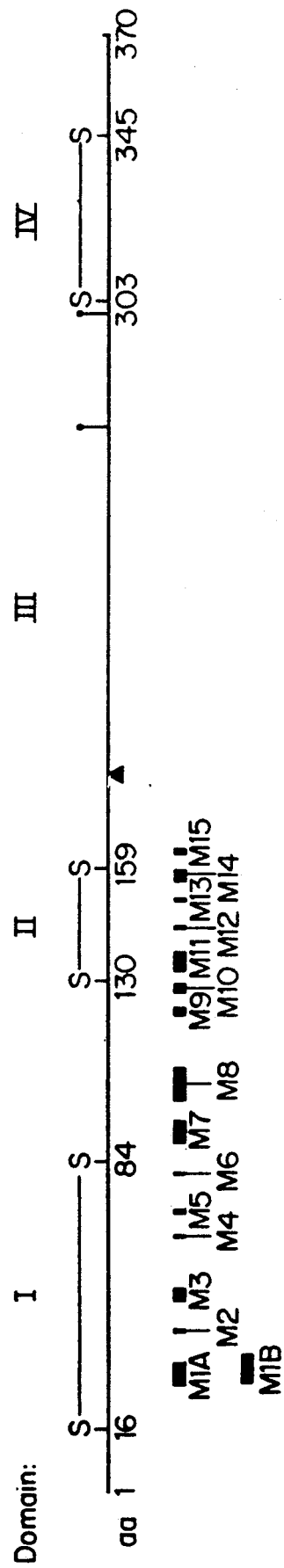
FIG. 2 is a schematic representation of CD4 protein $T4_{ex1}$ showing the four immunoglobulin-like domains, three disulfide bonds and two potential glycosylation sites. Numbering of amino acids is according to Hussey et al., Nature, 331:78-81 (1988). The positions of 16 mutations (see the Table) are represented below the line. The triangle indicates a stop codon introduced by site directed mutagenesis to create a protein containing only the first 182 amino acids.

Residues of the CD4 structure involved in gp120 binding were characterized through use of a Cos-cell expression system and a cDNA encoding the anchorminus CD4 segment termed $T4_{ex1}$ Hussey, R. E., et al., Nature, 331: 78-81 (1988) The 370 amino acid $T4_{ex1}$ protein (FIG. 1) contains 369 of the predicted 372 NH$_2$-terminal amino acids of the CD4 extracellular segment and a COOH-terminal histidine. As shown in FIG. 2, this structure is comprised of three intrachain disulfide bonded domains (a domain is defined as residues between and including 20 amino acid residues to either side of the cysteines), and one domain (III) which lacks cysteine residues but, like its counterparts, is immunoglobulin-like. Clark, S., et al., Proc. Natl. Acad. Sci. USA, 84: 1649-1653 (1987). Nanomolar concentrations of $T4_{ex1}$ inhibit gp120-transmembrane CD4 interaction, syncytium formation and HIV infection by binding to gp120-expressing cells. Hussey, R. E., et al., Nature, 331: 78-81 (1988).

As described in Example 1, the $T4_{ex1}$ construct was subcloned into the vector CDM8 and transfected into Cos-1 cells Seed, B., et al., Proc. Natl. Acad. Sci. USA, 84: 3365-3369 (1987) Supernatants from metabolically labelled transfected cells were tested by immunoprecipitation with an anti-CD4 monoclonal antibody (19Thy5D7). The resulting precipitate was subjected to SDS-PAGE. Results showed the presence of a 50KD CD4-derived molecule in transfected Cos-1 cell supernatants (FIG. 3, lane 3). The same molecule is co-precipitated from Cos-1 supernatants with an anti-gp120 monoclonal antibody after preincubation of the supernatant with gp120 (FIG. 13, lane 5). These reactions are specific for $T4_{ex1}$, as demonstrated by the fact that an irrelevant antibody (anti-T8) fails to precipitate $T4_{ex1}$ (FIG. 3, lane 1) and 2) no CD4 band is detected with anti-gp120 antibody in the absence of gp120 (FIG. 3, lane 6).

Prior studies employing either CD4 DNA truncation or proteolytic digestion demonstrated that the residues critical for gp120 interaction reside in domains I and/or II exclusively. Traunecker, A., et al., *Nature*, 331: 84–86 (1988); Berger, E. A., et al., *Proc. Natl. Acad. Sci. USA*, 85: 2357–2361 (1988) (Richardson, N. E., et al., *Proc. Natl. Acad. Sci. USA*, in press) Similarly, the Cos-1 cell derived product of a $T4_{ex1}$ protein truncated after amino acid residue 182 (by insertion of a stop codon in the cDNA sequence) is precipitated as a 20KD protein by anti-CD4 antibody and binds to gp120 (FIG. 3, lanes 4 and 7, respectively). In contrast, expression of a cDNA truncated at amino acid 110 (containing domain I only) failed to give rise to a gp120 binding protein. (Example 1) These data suggest that both domain I and II are required for gp120 binding.

Therefore, further analysis of the CD4-gp120 interaction was carried out by creating 35 amino acid substitutions which encompass all non-conservative mouse-human species differences within the first two domains of CD4 between amino acid residues 26 and 167. The $NH_2$-terminal CD4 amino acids were not considered here because an $NH_2$-terminal synthetic peptide failed to block gp120 binding even at millimolar concentrations. For each substitution, an amino acid of the human sequence was replaced with the amino acid found in the equivalent position of the murine CD4 sequence. Maddon, P. J., et al., *Proc. Natl. Acad. Sci. USA* 84: 9155–9159 (1987). The murine CD4 sequence does not bind gp120, and, thus, it was anticipated that some murine substitutions would abrogate human CD4-gp120 interaction. As shown in the Table, 15 oligonucleotides were used in a standard site-directed mutagenesis protocol, as described in Example 1, to produce 16 different versions of the human CD4 molecule containing from 1–4 substitutions each. The positions of these substitutions are listed in the Table and diagrammatically mapped in FIG. 2. All 16 CD4 mutants were assayed after transfection into Cos-1 cells by immunoprecipitation with anti-CD4 monoclonal antibody and by gp120 co-precipitation with anti-gp120.

TABLE 1
PRODUCTION AND ANALYSIS OF CD4 SITE-DIRECTED MUTANTS

| Mutant | Oligonucleotide used for mutagenesis | Amino acid change | Anti-CD4 immuno-precipitation | Anti-gp120 co-precipitation |
|---|---|---|---|---|
| M1A | Mouse subst.   T   F   D   I[a]<br>223 CAA—TTC—ACC—TGG—AAA—TTC—TCC—GAC—CAG—AGA—AAG 255<br>Human aa   H   N   N   I | aa 27 H to T<br>aa 30 N to F<br>aa 32 N to D | + | + |
| M1B |        T   F   D   R<br>223 CAA—TTC—ACC—TGG—AAA—TTC—TCC—GAC—CAG—AGA—AAG 255<br>       H   N   N   I | aa 27 H to T<br>aa 30 N to F<br>aa 32 N to D<br>aa 34 I to R | + | + |
| M2 |            H<br>261 G—GGA—AAT—CAC—GGC—TCC 276<br>           Q | aa 40 Q to H | + | + |
| M3 |          G   P   S<br>283 ACT—AAA—GGT—GGA—TCC—CCG—AGT—AAT—GAT—CG 311<br>         P   K   L | aa 48 P to G<br>aa 50 K to P<br>aa 51 L to S | + | – |
| M4 |      K<br>335 GG—GAC—AAA—GGA—AAC—TTC 351<br>     Q | aa 64 Q to K | + | + |
| M5 |            N   K<br>355 CTG—ATC—ATC—AAT—AAG—CTT—AAG 375<br>           K   N | aa 72 K to N<br>aa 73 N to K | + | + |
| M6 |         Q<br>382 GAC—TCA—CAG—ACT—TAC—ATC 399<br>        D | aa 80 D to Q | + | + |
| M7 |      N   R                 E<br>406 GTG—GAG—AAC—CGG—AAG—GAG—GAG—GTG—GAA—TTG—C 436<br>     D   Q                 Q | aa 88 D to N<br>aa 89 Q to R<br>aa 94 Q to E | + | + |
| M8 |         K                 P             S<br>436 CTA—GTG—TTC—AAA—TTG—ACT—GCC—CCT—GAC—ACC—AGC—CTG—CTT—C 478<br>        G                 S             H | aa 99 G to K<br>aa 104 S to P<br>aa 107 H to S | + | + |
| M9 |         S   K   V<br>499 ACC—TTG—GAG—AGC—AGC—AAG—GTT—AGT—AGC—CCC 528<br>        P   P   G | aa 121 P to S<br>aa 122 P to K<br>aa 123 G to V | + | –[c] |
| M10 |         L      T        E<br>520 AGT—AGC—CCC—CTA—ACG—GAA—TGT—AGG 543<br>        S      V      Q | aa 127 S to L<br>aa 128 V to T<br>aa 129 Q to E | + | + |
| M11 |        H   K                          V<br>534 G—CAA—TGT—AGG—CAT—AAA—AGG—GGT—AAA—GTC—ATA—CAG—GG 569<br>       S         P                        N | aa 132 S to H<br>aa 133 P to K<br>aa 137 N to V | + | + |

TABLE 1-continued
PRODUCTION AND ANALYSIS OF CD4 SITE-DIRECTED MUTANTS

| Mutant | Oligonucleotide used for mutagenesis | Amino acid change | Anti-CD4 immuno-precipitation | Anti-gp120 co-precipitation |
|---|---|---|---|---|
| M12 | 570 G—GGG—AAG—GTC—CTC—TCC—G 586<br>                V<br>                T | aa 143 T to V | + | + |
| M13 | 590 CT—CAG—CTG—CGG—CTC—CAG—G 607<br>               R<br>               E | aa 150 E to R | + | + |
| M14 | 606 G—GAT—AGT—GAC—TTC—TGG—AAT—TGC—ACT—GTC 633<br>        D      F              N<br>        G      T              T | aa 155 G to D<br>aa 156 T to F<br>aa 158 T to N | −[b] | −[c] |
| M15 | 626 GC—ACT—GTC—ACG—CTG—GAC—CAG—AAG 648<br>        T     L      D<br>        L     Q      N | aa 162 L to T<br>aa 163 Q to L<br>aa 164 N to D | + | + |

[a]Two mutants were recovered from the mutagenesis using this oligonucleotide; one contained mutations at amino acid 27, 30 and 32 but not 34 and the second contained all four changes. These two mutants were transfected separately.
[b]M14 was also negative when tested for immunoprecipitation with anti-CD4 monoclonal OKT4A.
[c]A very faint 50 KD band (~10 fold less intense than T4$_{exl}$) was observed upon coprecipitation with gp120.
Mutagenesis, immunoprecipitation and coprecipitation procedures are described in the legend to FIG. 1.

Figure 4A:
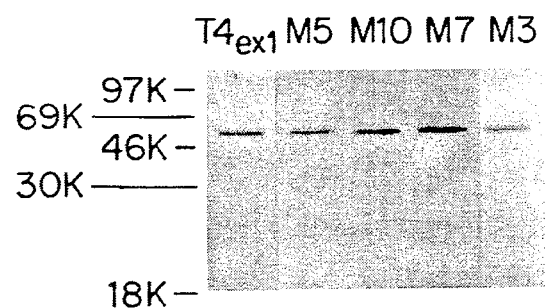
FIG. 4 (parts a and b) shows results of anti-CD4 immunoprecipitation of $^{35}$S-cysteine labelled supernatants from Cos-1 cells transfected with $T4_{ex1}$, M5, M10, M7 and M3 (panel b). Precipitations were carried out in the presence (+) or absence (−) of gp120.
Figure 4B:
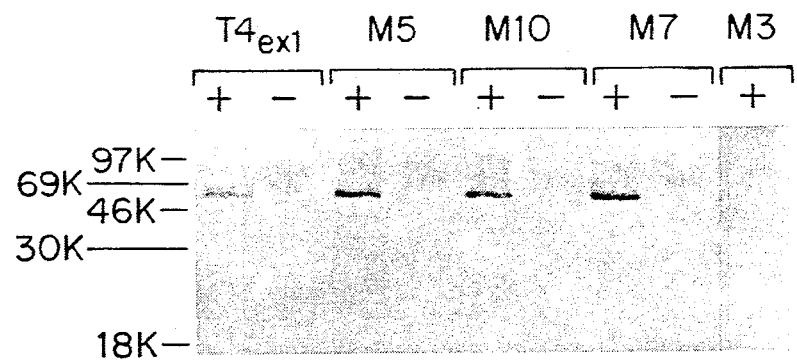

Immunoprecipitation of the original T4$_{ex1}$ and four representative mutants is shown in FIG. 4 (panel a). In addition to T4$_{ex1}$, each of the mutants M5, M10, M7 and M3 react with the anti-CD4 monoclonal antibody 19Thy5D7. As shown in the Table, 15 of the 16 mutants react with anti-CD4 antibody. Only mutant M14 did not react; it was also unreactive with OKT4A, which is a second monoclonal antibody directed at a different CD4 epitope.

Thirteen of the 16 mutants bound gp120 in a manner equivalent to T4$_{ex1}$ as judged by the co-precipitation assay. FIG. 4 (panel b) demonstrates that T4$_{ex1}$, M5, M10 and M7 are all co-precipitated by anti-gp120 in the presence of gp120. Overall, a 2-3 fold experimental variation in co-precipitation with gp120 was observed (T4$_{ex1}$ vs. M5 in panel b FIG. 4). Among gp120 binding CD4 proteins, however, a positive signal was observed in every experiment (using a minimum of 2-3 separate transfections). In contrast, although M3 is recognized by anti-CD4 antibody, it fails to bind to gp120 (FIG. 4, panel b). In addition, M9 (Table) has a substantially reduced gp120 binding capacity, although anti-CD4 monoclonal antibody immunoprecipitates a band of identical size and intensity to T4$_{ex1}$. M3 contains three amino acid substitutions in human CD4 domain I at positions 48, 50 and 51. One or more of these changes clearly abrogates the ability of CD4 to bind to gp120. M9 contains three amino acid substitutions in domain II of CD4 at positions 121-123. Thus, alteration of a few residues in either CD4 domain I or domain II results in abrogation of gp120 binding.

In addition, M14 demonstrates reduced binding to gp120 (Table). M14 also failed to bind to the two anti-CD4 monoclonal antibodies examined. Thus, one cannot rule out the possibility that the three substitutions in M14 (at positions 155, 156 and 158) somehow decrease the expression of this mutant CD4 protein. It is more likely that these substitutions have destroyed both the gp120 binding site and the epitopes recognized by the two monoclonal antibodies, perhaps through a general disruption of the CD4 protein's 3-dimensional structure because translation of in vitro transcribed RNA from M14 gave results identical to T4$_{ex1}$ transcribed RNA.

The contribution of CD4 domain 1 to gp120 binding was recognized previously in studies of the T4$_{ex1}$ polypeptide produced in a baculovirus system in conjunction with proteolytic fragmentation analysis, microsequencing and a specific CD4-gp120 binding assay. Richardson, N. E., et al., *Proc. Natl. Acad. Sci. USA,* in press. Richardson and co-workers showed that disruption of the peptide bond at lysine 72 by tryptic cleavage destroyed CD4-gp120 interaction without inducing any detectable alterations in other domains of CD4. Furthermore, reduction of intrachain disulfide bonds in the CD4 molecule also abrogated high affinity gp120 binding, thereby strongly implying that the binding site for gp120 is complex and depends on the stabilized CD4 structure. Whether the domain I and II mutations introduced in the work described herein affect gp120 contact residues themselves or, alternatively, affect the tertiary structure around the contact residues cannot be concluded at present. Footprint analysis of CD4-gp120 protein-protein interactions or analysis of CD4-gp120 cocrystals will be necessary to determine the effect of the mutations described. Nevertheless, the ability of a synthetic peptide comprising amino acid residues 23-56 to inhibit syncytium formation at $10^{-4}$ M may support the notion that residues 48, 50 and/or 5 contribute to the gp120 binding sites. Jameson, B. A., et al., *Science,* 240: 1335-1339 (1988)

Eight residues are conserved between domain I of CD4 and the 14 invariant residues of the Kappa light chain variable (V) regions. Maddon, P., et al., *Cell,* 42: 93-104 (1985). In addition, the first and second cysteines (amino acids 16 and 84) in domain I of CD4 are separated by 67 amino acids, positions and spacing similar to those of members of the immunoglobulin family. Furthermore, secondary structural prediction suggests the presence of eight Kappa strands in CD4 domain I. In light of these homologies to Ig, CD4 domain I was modelled on the basis of the known 3-dimensional coordinates of the $V_k$ Bence-Jones homodimer, REI. Use of this model has resulted in accurate prediction of each of three tryptic cleavage sites in domain I to be surface exposed thus supporting the validity of the CD4 model. Richardson, N. E., et al., *Proc. Natl. Acad. Sci. USA,* in press. It was therefore of interest to determine the relative positions of the M3 mutations at amino acid residues 48, 50 and 51 of CD4.

Figure 5:
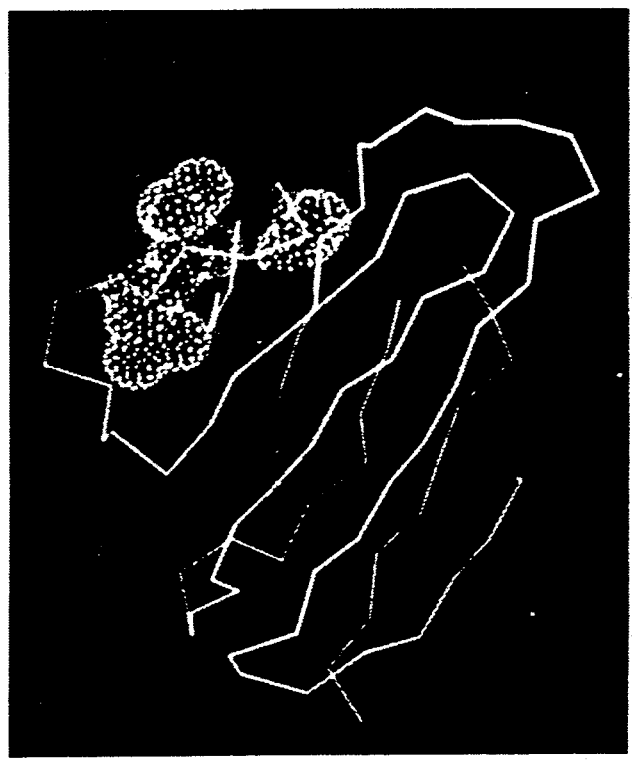
FIG. 5 shows the location of amino acid residues in domain I of CD4 predicted to be involved in gp120 binding. Alpha carbon skeleton of a $V_K$ domain is derived from coordinates of the Bence-Jones homodimer REI. See Epp, O. et al., Biochem., 14:4943-4952 (1975). One member of the dimer is shown. Spheroids indicate residues in REI corresponding to the region of amino acid substitutions in mutant M3. The alignment of CD4 and REI is similar to that of Maddon et al. beginning at residue 8 of REI. Maddon, P. et al., Cell, 42:93-104 (1985). Diagrams were generated using an Evans and Sutherland PS-300 and the program Frodo. Jones, T. A., J. Appl. Cyst., 11:268 (1978). The dyad of the immunoglobulin variable domain is vertical with the "hypervariable" loops at the top right of the photograph.

FIG. 5 shows the alpha carbon skeleton of one chain of the REI homodimer. The region of residues in REI corresponding to the mutated CD4 residues which abrogate gp120 binding are highlighted by spheroids. This region corresponds to the C" strand unique to V domains which connect the two sheets. Williams, A. F., et al.. *Ann. Rev. Immunol.,* 6, 381-405 (1988). The alignment between REI and CD4 requires a gap in this segment, and, thus, it is not meant to imply that the CD4 alpha carbon skeleton follows an identical course in this region. Nevertheless, it is very likely that the CD4 sequence will loop out and be solvent exposed. Furthermore, note that this site is distinct from the three segments equivalent to the hyper-variable loops which are located at the top (right) of FIG. 5. Based on the above analysis, one prediction would be that if gp120 does contact residues in the region analogous to the C" strand of REI, it might also contact residues in CD4 domain II adjacent to this region. Perhaps M9 and/or M14 mutations are localized to such sites. That domains I and II of CD4 might be spatially close to one another in some regions is further supported by antibody competition studies in which an antibody (OKT4A) whose epitope was mapped to a region in domain I showed reciprocal competitive binding with two antibodies (OKT4F and OKT4B) whose epitopes mapped to domain II. Jameson, B. A., et al., *Science,* 240: 1335-1339 (1988).

The region of CD4 domain I implicated as a possible binding site for gp120 is distinct from the loops analagous to hypervariable complementarity determining segments. If those loops form a binding site for class II MHC, the putative natural ligand of CD4 one can speculate that gp120 may be incapable of inhibiting class II recognition events, even after binding to the CD4 structure. Krensky, A. M., et al., *Proc. Natl. Acad. Sci. USA,* 79: 2365-2369 (1982); Meuer, S. C., et al., *Proc. Natl. Acad. Sci. USA.* 79: 4395-4399 (1982); Biddison, W., et al., *J. Exp. Med.,* 156: 1064-1076 (1982); Marrach, P., et al., *J. Exp. Med.,* 158: 1077-1091 (1983); Doyle C., et al., *Nature,* 330: 256-259 (Ig8? ) The CD4 mutants described herein should be useful in future analysis of CD 4- class II MHC interactions.

As a result of the identification of sites critical to binding of CD4 to the HIV gp120 envelope protein, it is now possible to produce modified soluble human CD4 fragments whose ability to bind gp120 is altered (i.e., whose ability to bind gp120 is different from that of the corresponding naturally-occurring human CD4 fragment). As described in the previous sections and in the Examples, such sites have been identified by oligonucleotide-directed mutagenesis used to create 16 mutant human CD4 molecules which resulted in substitution of all non-conserved murine amino acid residues for human CD4 residues between amino acid positions 27-167, as represented in FIG. 1.

As shown in the Table, 15 of the 16 CD4 "mutants" created as described react with anti-CD4 monoclonal antibody 19thy5D7 and 13 of the 16 bind gp120 in a manner equivalent to the gp120 binding evidenced by T4$_{ex1}$. Three mutants, designated M3, M9 and M14, do not exhibit gp120 binding equivalent to that of T4$_{ex1}$: M3 fails to bind gp120; M9 has substantially reduced gp120 binding capacity; and M14 demonstrates reduced gp120 binding ability. As also shown in the Table, M3 and M9 are recognized by anti-CD4 antibody and M14 is not recognized by either of the two anti-CD4 antibodies used.

These results demonstrate that these sites are critical for gp120 binding by CD4 and that the changes made in the amino acid sequence of human CD4 (as represented in FIG. 1) to produce these CD4 mutants resulted in elimination of or reduction in gp120 binding. In a similar manner, other changes at one or more of these critical sites can result in elimination of or reduction in gp120 binding ability. Conversely, amino acid residues can be introduced at these critical sites to produce modified soluble human CD4 fragments with enhanced gp120 binding ability.

Such substitutions can be made: 1) at one, two or all three of the critical sites (i.e., at one or more of the three amino acid sites represented by mutants M3, M9 and M14) and/or 2) of one, two or all three amino acid residues within each site (i.e., within a critical site, of amino acid residues 1, 2 or 3 individually; 1, 2 and 3 in any combination of a 2 amino acid residues; or of all three amino acid residues).

For example, in mutant M3, glycine, proline and serine, respectively, replace proline, lysine and leucine, which occur at amino acid positions 48, 50 and 51 of human CD4. Substitution of one or more of those amino acids by other amino acids of the same type (e..g, at position 48 by another amino acid with a nonpolar R group) as that present at that position in M3 can be made and the effect on gp120 binding ability determined.

Substitutions at these three sites, individually or in combination, of amino acids having characteristics different from those of amino acid whose presence at those sites has been shown to eliminate or reduce gp120 binding ability can also be made and their effect on binding ability assessed using the anti-CD4 immunoprecipitation and anti-gp120 coprecipitation methods described in the Examples. In particular, substitutions of some or all of the amino acids at one or more of these critical sites which result in modified soluble CD4 fragments with enhanced gp120 binding ability can be made. Using the techniques described herein, CD4 fragments having enhanced binding ability can be identified.

One approach to producing modified soluble human CD4 fragments with enhanced gp120 binding ability is as follows: amino acid residues present at the three sites in human CD4 (as represented in FIG. 1) and amino acid residues present at the corresponding positions in the three mutant CD4 molecules are excluded from the group of amino acid residues to be assessed for their effects on gp120 binding ability when they are incorporated at these sites. Also excluded are amino acids having similar characteristics (e.g., nonpolar R groups, uncharged polar R groups, etc.). Mutants are then produced to include amino acid residues other than those eliminated from consideration in this manner. Each mutant is then assessed using the anti-CD4 immunoprecipitation and anti-gp120 coprecipitation techniques described.

As a result, modified soluble human CD4 fragments having enhanced gp120 binding ability can be identified. Similar techniques can be used to identify additional critical sites, if such sites exist, and, subsequently, to make substitutions and assess their effects on gp120 binding ability of the resulting modified soluble CD4 fragments.

Production of Modified Soluble CD4 Fragments Having Altered gp120 Binding Ability Modified soluble CD4 fragments having altered gp120 binding ability are produced using the techniques described in detail in the Examples. Briefly, they are produced as follows:

DNA encoding a desired CD4 fragment is produced, either by using recombinant DNA techniques, such as excising it from a vector containing cDNA encoding such a fragment, or by synthesizing DNA encoding the desired fragment mechanically and/or chemically, using known techniques. DNA produced by these techniques encodes a soluble CD4 fragment which includes none of the hydrophobic transmembrane region of CD4 or a portion of that region (generally six amino acids or less) small enough that it does not prevent solubilization of the fragment. DNA produced in this way can be, for example, DNA encoding a modified soluble human CD4 fragment which is capable of binding HIV gp120 envelope protein and which consists essentially of domain I and domain II CD4 protein. Such DNA can encode a modified soluble human CD4 fragment which has altered (reduced or enhanced) gp120 binding ability. In addition, particularly in the case of CD4 fragments having enhanced gp120 binding ability, the CD4 fragment is long enough (e.g., 10 amino acids or more) to bind effectively to HIV gp120 envelope protein. In this case, DNA encoding a modified soluble human CD4 fragment having enhanced gp120 binding ability is produced; this DNA encodes such a CD4 fragment which is of sufficient length to bind effectively to HIV gp120 envelope protein. In this case, DNA encoding a modified soluble human CD4 fragment having enchanced gp120 binding ability is produced; this DNA encodes such a CD4 fragment which is of sufficient length to bind effectively to HIV gp120 envelope protein.

Templates for subsequent mutagenesis are produced, using the CD4 fragment-encoding cDNA or DNA. As described below, this can be carried out using a single-stranded bacteriophage cloning vehicle, such as M13. This results in production of single-stranded DNA homologous to only one of the two strands of the DNA encoding the desired CD4 fragment. The resulting single-stranded DNA is used as a template for producing the desired modified soluble CD4 fragments, as follows:

Oligonucleotides are produced, such that their sequence includes a base change or changes which, when incorporated into the nucleotide sequence of DNA subsequently used for the production of CD4 fragments, results in the desired change in the encoded CD4 protein (i.e., different from that encoded by the nucleotide sequence of FIG. 1). Such oligonucleotides are produced using standard methods. Oligonucleotides having a base change or base changes are referred to as mutagenized or mutant oligonucleotides.

The mutant oligonucleotide produced in this manner is hybridized to (e.g., by being kinased) the template produced as described above, to produce a template-mutant oligonucleotide complex, referred to as a mutant primer/template. The mutant primer/template is used for the production of a second strand of DNA, using well-known techniques. For example, synthesis of the second DNA strand is carried out by the Klenow fragment of DNA polymerase in the presence of dCTPαS. Taylor, J. W. et al., *Nucleic Acids Research*, 13:8749–8764 (1985); Taylor, J. W. et al., *Nucleic Acids Research*, 13:8764–8785 (1985); Nakayame, K. and F. Eckstein, *Nucleic Acids Research*, 14:9679–9698 (1986). The resulting strand of DNA contains a modification (or modifications) in the nucleotide sequence of T4 cDNA (i.e., is different from the nucleotide sequence represented in FIG. 1) and is referred to as a mutant strand.

Unreplicated single-stranded DNA is removed and the double-stranded DNA is nicked with a selected restriction enzyme (e.g., NciI, which does not cut phosphorothioate DNA and, thus, does not cut the new DNA strand containing dCTαS or the mutant strand). Nicked, nonmodified DNA is removed by digestion with another enzyme, such as exonuclease III. The resulting gapped DNA is repolymerized and, because the mutant strand serves as the template for repolymerization, the mutation or modification is copied into both strands.

Once produced, the double-stranded DNA, in which both strands contain the mutation or modification encoding the corresponding modification in the amino acid sequence of the desired soluble CD4 fragment is introduced into a competent host cell, such as a competent bacterial host (e.g., by transformation). The resulting plaques are grown and DNA contained in them is isolated, using known techniques, and sequenced to confirm the presence of the mutation.

The mutated DNA produced in this manner is excised from the M13 vector containing it, introduced into a suitable expression vector, such as CDM8, and transfected into an appropriate host cell, such as Cos cells, in which it is expressed. Aruffo, A. and B. Seed, *Proceedings of the National Academy of Sciences, USA*, 84:3365–3369 (1987). As a result, mutant CD4 proteins can be assayed, using known techniques. The vector-insert ligation mixture is introduced into competent host bacteria, such as the publicly available *E. coli* MC1061 P3, and radiolabelled T4 DNA is used to identify CDM8 containing mutant T4 cDNAs.

Production, in Cos cells transfected with the vector containing mutant T4 cDNA, of modified soluble CD4 fragments having the desired alteration in gp120 binding ability is subsequently assayed, using known techniques described below.

As a result of this procedure, double stranded DNA encoding a modified soluble CD4 fragment having altered gp120 binding ability is produced, the encoded CD4 fragment is expressed and its ability to bind the HIV gp120 envelope protein is assessed.

An alternative approach to producing modified soluble human CD4 fragment having altered gp120 binding ability is to use peptide synthesis to make a peptide or polypeptide having the amino acid sequence of such a fragment.

The above-described technique was used for producing the 16 mutant CD4 fragments whose sequences are represented in the Table. Construction of the 16 mutants, transfections, immunoprecipitations and co-precipitations were carried out as described in Example 1. The presence of each mutant was confirmed by directly sequencing the plasmid DNA used for individual transfections.

Applications of Modified Soluble CD4 Fragments Having Altered gp120 Binding Ability As described in co-pending U.S. patent applications Ser. Nos. 206,585 (filed June 14, 1988); 106,1 85 (filed Oct. 8, 1987); and 144,31 3 (filed Jan. 14, 1988), the teachings of which are incorporated herein by reference, soluble CD4 fragments encoded by the nucleotide sequence represented in FIG. 1 did not inhibit Class II MHC recognition events (failed to inhibit CTL effector function), even at high concentrations. As also described in the cited applications, the soluble CD4 fragments had no discernible effect on Class II-directed physiologic T cell responses, despite the fact that they bind HIV gp120 and inhibit binding of gp120 to the CD4 molecule, inhibit HIV envelope-induced syncytium formation and HIV replication. For example, they were shown to have no effect on proliferation of the T4 tetanus toxoid specific, class II MHC restricted helper T cell clone CTT7.

It is reasonable to assume that the modified soluble CD4 fragments of the present invention with enhanced gp120 binding ability will be shown to have the same advantage. That is, it is reasonable to assume such fragments of the present invention have the capacity to bind the HIV gp120 envelope protein and interfere with HIV infection of T cells, but will not interfere with the function or proliferation of human T lymphocytes which are not infected with HIV. The capability of fragments to bind gp120 envelope protein and interfere with HIV infection and their lack of interference with uninfected T lymphocytes can be assessed by means described in the cited co-pending applications, using known techniques.

Modified soluble human CD4 fragments of the present invention can be used for therapy, diagnosis and prevention of infection by HIV.

For example, use of fragments having slightly reduced or turned down affinity may improve the effective pharmokinetics of therapy. For example, such fragments can be used to bind or hold on to gp120 (and, thus, HIV) transiently. Such fragments bind the virus long enough to render it ineffective as an infectious agent and to prepare it to bind or accept another therapeutic agent (e.g., one which will destroy the virus).

In addition, the region of the CD4 domain I implicated as a possible binding site for gp120 is distinct from the loops analogous to hypervariable complementarity determining segments. If those loops form a binding site for class II MHC, the putative natural ligand of CD4, one can speculate that gp120 may be incapable of inhibiting class II recognition events, even after it has bound to the CD4 structure. Thus, the CD4 mutant described herein should be useful in future analysis of CD4 class II MHC interactions.

Fragments of the present invention having enhanced gp120 binding ability can be used therapeutically (in vivo) to treat individuals infected with HIV. Such fragments can be administered by an acceptable route (e.g., intravenously, intramuscularly, intraperitoneally, orally), alone or after combination with an acceptable carrier (e.g., saline buffer). Modified soluble CD4 fragments with enhanced gp120 binding ability of the present invention can be administered to inhibit binding of HIV to T4 lymphocytes and to inhibit HIV transmission from an infected cell to uninfected cells by interfering with syncytium formation. The quantity of such CD4 fragments administered will be determined on an individual basis, but will generally range from approximately 10 ug/kg body weight to approximately 500 ug/kg body weight per day (in one or more doses per day).

Modified soluble CD4 fragments having enhanced gp120 binding ability can also be used for diagnostic purposes. Because of their enhanced binding ability, they can be used in known immunoassay procedures for detecting the presence and determining the quantity, if desired, of HIV gp120 envelope protein (and, as a result, of HIV itself) in samples, such as blood, semen and saliva. CD4 fragments of the present invention can be, for example, attached or bound by virtue of the CD4 fragment to solid support, such as latex beads, which are then contacted with a sample to be assayed, in such a manner that if HIV is present in the sample, it will be bound (by virtue of the CD4 fragment-gp120 interaction). This can be followed by precipitation and/or labelling through contact with an anti-gp120 antibody and detection of the precipitate or labelled product, using known techniques.

Modified soluble CD4 fragments having enhanced gp120 binding ability can also be used for the prevention of HIV infection. For example, such fragments can be incorporated in or attached to materials which might come in contact with HIV. They can be incorporated into spermicides; incorporated into or attached to surfaces of condoms, materials from which surgical gloves, dressings and other medical equipment are made; or attached to the surfaces of containers or other materials (e.g., filters) for receiving, processing and/or storing blood. In each case, the CD4 fragments of the present invention will bind to HIV gp120 envelope protein (and, thus, to HIV), which will be prevented from further passage (e.g., in the case of spermicides, condoms, surgical gloves, dressings) or can be removed (e.g., in the case of donated or stored blood).

This invention will now be illustrated by the following Examples, which are not to be seen as limiting in any way.

EXAMPLE 1

Production of Modified Soluble Human CD4 Fragments

Methods: The 1.17Kb $T4_{ex1}$ fragment was excised using BamHI from pAC 373/$T4_{ex1}$, blunted using the Klenow fragment of DNA polymerase I, ligated to XhoI linkers (New England Biolabs) and subcloned in the XhoI site of the vector CDM8. Hussey, R. E. et al., *Nature*, 330:487-489 (1987); Seed, et al., *Proc. Natl. Acad. Sci. U.S.A.*, 84:3365-3369 (1987) For transfection of CDM8 constructs into Cos cells, 2-3 ×$10^6$ cells are plated in 100×15 cm dishes in RPMI 1640 (Gibco) containing 10% fetal bovine serum (FBS). Twelve to twenty-four hours later, 45 ug of plasmid DNA are added to 2.5 ml RPMI and mixed with 2.5 ml RPMI-800 ug/ml DEAE dextran, then added to the washed Cos cells. After approximately 2 hours at 37° C., the cells are washed and then incubated in RPMI containing 2% FCS, 1% glutamine, 1% penicillin-streptomycin, 10 ug/ml gentamycin and 150 uM chloroquine for 3 hours. The cells were incubated at 37° C. for 2 days in RPMI 10% FCS. For metabolic labelling, the transfected Cos cells (2 days after transfection) and incubated for 1 hour in 5 ml RPMI minus cysteine containing 10% FCS. The media is removed and the cells are incubated in RPMI minus cysteine containing 10% dialyzed FCS and 100 uCi/ml of $^{35}$S-cysteine for 5-6 hours at 37° C. The supernatants are removed, centrifuged at 200 g for 10 minutes and dialyzed vs. PBS/0.025% azide/10mM col cysteine overnight at 4° C. For immunoprecipitation, 5 ml of the dialyzed $^{35}$S-cysteine labelled supernatant is precleared by a 45 minute incubation at 4° C. with 20 ul anti-T8 antibody (21 Thy2D3) on Affigel-10 (Biorad) beads (about 5 mg antibody per ml beads). The precleared supernatant is then incubated with 20 ul anti-CD4 (19Thy5D7) on Affigel-10 beads for 3 hours at 4° C. The beads are washed once in 10 ml 10 mM Tris, pH 6.8/0.1 % Triton X-100/0.1% SDS/0.5% DOC, once in ±1 ml of the same buffer and once in 1 ml 0.1 M glycine, pH 5/0.1 % Triton X-100 and then eluted with 35 ul 0.1 M glycine, pH 2/0.1 % Triton X01 00 and neutralized with 6 ul 1 M Tris, pH 7.6. The sample is run on a 0.75 or 1.5 mm 12.5% mini-polyacrylamide-SDS gel under non-reducing conditions. The gel is fixed, dried and autoradiographed at about 70° C. from 1–7 days. Immunoprecipitation with anti-CD8 was carried out as above except that 20 ul anti-CD8 on Affigel-10 beads is used for immunoprecipitation. For co-precipitation with gp120 (kind gift of Dr. Bolognesi, Duke University), 0.5 ml of labelled supernatant is incubated with 67 ng native gp120 for 2 hours at 37° C. Five hundred ng anti-gp120 (Dupont) and 10 ul rabbit anti-mouse IgG Sepharose 4B beads are added and rotated for 2 hours at 4° C. The beads are washed once in 10 ml and once in 1 ml cold PBS, eluted and the sample run in SDS-PAGE as above.

The CD4 protein (182 amino acids long) was created using the thionucleotide method of oligonucleotide site directed mutagenesis. Taylor, J. W. et al., *Nucl. Acids Res.*, 13:8749-8765 (1985); Taylor, J. W. et al., *Nucl. Acids Res.* 13:8765-8785 (1985); Nakayame et al., *Nucl. Acids Res.* 14:9679-9698 (1986) The XhoI insert of $T4_{ex1}$ was excised from CDM8, blunted with the Klenow fragment of DNA polymerase I ligated to XbaI linkers (New England Biolabs) and subcloned into M13mp18. Single stranded DNA was prepared as a template and mutagenesis was carried out according to the manufacturer's recommendations (Amersham). For the 182 amino acid truncation, the oligonucleotide 5, GAAGGCCTAAAGCATAG 3' was synthesized using standard cyanoethyl phosphoramodite chemistry. The termination codon which converts the serine (TCC) at amino acid 183 to a stop codon is underlined. The presence of the mutation was confirmed by sequencing the M13mp18-T4 construct and mini preps of the replicative form of the mutation-containing DNA were prepared. The mutated insert was excised with XbaI and ligated into the XbaI site of CLM8. The presence of the mutation was then directly confirmed by sequencing the CDM8-T4 insert using the double stranded DNA as a template. Although not shown, a truncation was also created at amino acid 110 using the oligonucleotide CACCTGCTTTAGGGGCAG.

EXAMPLE 2

Production and Analysis of CD4 Site-Directed Mutants

16 CD4 mutants were constructed, as described in Example 1. As shown in the Table, 15 oligonucleotides were used, in a standard site-directed mutagenesis protocol (Example 1), to produce 16 different version of the human CD4 molecule, each containing from 1 to 4 amino acid substitutions. As a result, the amino acid residue normally present in human CD4 protein at the position indicated in the Table (See FIG. 1) was replaced by the amino acid present in the equivalent position of the murine CD4 sequences.

Three mutants, M3, M9 and M14, evidenced altered gp120 binding ability: M3 failed to bind gp120, M9 has substantially reduced gp120 binding capacity and M14 also demonstrates reduced gp120 binding capacity. The amino acid substitutions made in each are as follows:

| | |
|---|---|
| M3 | amino acid 48:P changed to G |
| | amino acid 50:K changed to P |
| | amino acid 51:L changed to S |
| M9 | amino acid 121:P changed to S |
| | amino acid 122:P changed to K |
| | amino acid 123:G changed to V |
| M14 | amino acid 155:G changed to D |
| | amino acid 156:T changed to F |
| | amino acid 158:T changed to N |

P: proline
K: lysine
L: leucine
G: glycine
T: threonine
S: serine
V: valine
D: aspartic acid
F: phenylalanine
N: asparagine

Equivalents

Those skilled in the art will recognize, or be able to ascertain, using no more than routine experimentation, many equivalents to the specific embodiments of the invention described specifically herein. Such equivalents are intended to be encompassed in the scope of the following claims.

We claim:

1. DNA encoding a modified human CD4 molecule with increased or decreased HIV-1 gp120 binding ability compared to the native human CD4 molecule wherein said modified CD4 molecule consists essentially of a native human CD4 molecule from which has been deleted the cytoplasmic and transmembrane regions and wherein said truncated CD4 molecule contains one or more of the following amino acid substitutions.

amino acid 48 of the human truncated CD4: P changed to G
amino acid 50 of the human truncated CD4: K changed to P
amino acid 51 of the human truncated CD4: L changed to S
amino acid 121 of the human truncated CD4: P changed to S
amino acid 122 of the human truncated CD4: P changed to K
amino acid 123 of the human truncated CD4: G changed to V
amino acid 155 of the human truncated CD4: G changed to D
amino acid 156 of the human truncated CD4: T changed to F
amino acid 158 of the human truncated CD4: T changed to N.

* * * * *

UNITED STATES PATENT AND TRADEMARK OFFICE
CERTIFICATE OF CORRECTION

PATENT NO. : 5,109,123

DATED : April 28, 1992

INVENTOR(S) : Ellis L. Reinherz, et al

Figure 3B:
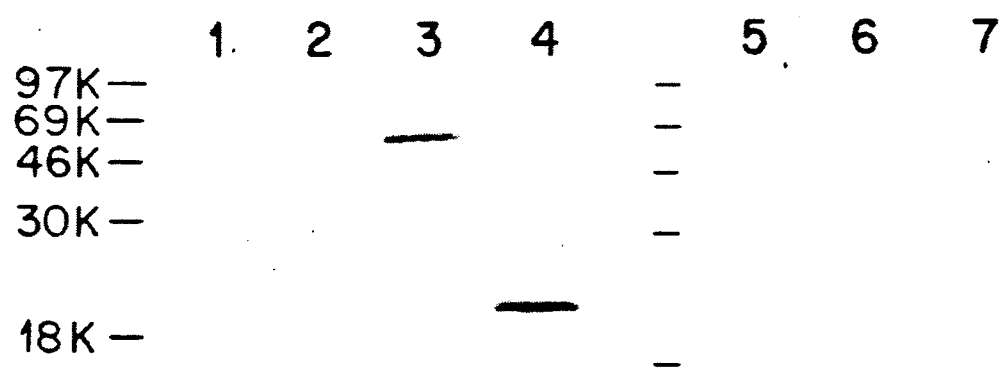
FIG. 3b shows results of anti-CD4 immunoprecipitation and anti-gp120 co-precipitation of $T4_{ex1}$ and a truncated 182 amino acid version of CD4 from supernatants of $^{35}$S-cysteine labelled Cos-1 cells transfected with the CD4 constructs. Lane 1, immunoprecipitation of supernatant from Cos-1 cells transfected with the $T4_{ex1}$ containing plasmid and immunoprecipitated with anti-T8 (21 Thy2D3) (control); lane 2, immunoprecipitation of supernatant from Cos-1 cells transfected with the 182 amino acid truncation using the control anti-T8 antibody; lane 3, immunoprecipitation of $T4_{ex1}$ with anti-CD4 antibody (19Thy5D7); lane 4, immunoprecipitation of the 182 amino acid truncation of $T4_{ex1}$ with anti-CD4; lane 5, co-precipitation of $T4_{ex1}$ with anti-gp120 (Dupont) in the presence of gp120; lane 6, co-precipitation of $T4_{ex1}$ with anti-gp120 in the absence of gp120; lane 7, co-precipitation of the 182 amino acid truncation of $T4_{ex1}$ with anti-gp120 in the presence of gp120. All samples are run non-reduced. The molecular weight markers are phosporylase B (97.4KD), bovine serum albumin (69KD), ovalbumin (46KD), carbonic anhydrase (30KD), lactoglobulin A (18.4KD).

It is certified that error appears in the above-identified patent and that said Letters Patent is hereby corrected as shown below:

In the Drawings, sheet 7 of 9,
"FIG. 3b" should be --FIG. 3--.

Column 3, line 20, "FIG. 3b" should be --FIG. 3--.

Signed and Sealed this

Twenty-fourth Day of August, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,109,123

DATED : April 28, 1992

INVENTOR(S) : Ellis L. Reinherz and Linda K. Clayton

It is certified that error appears in the above-identified patent and that said Letters Patent is hereby corrected as shown below:

Column 1, line 3, before the subheading "Related Applications" the following subheading and sentences should be inserted:

---Government Support

This invention was made with government support under Grant No. AI27336 by the National Institutes of Health. The government has certain rights in the invention.---

Signed and Sealed this

Twentieth Day of December, 1994

Attest:

BRUCE LEHMAN

*Attesting Officer*            Commissioner of Patents and Trademarks